(12) United States Patent
Mork

(10) Patent No.: US 6,917,897 B2
(45) Date of Patent: Jul. 12, 2005

(54) FOOD AND EXERCISE CALCULATOR

(75) Inventor: Daniel L. Mork, Edgewater, MD (US)

(73) Assignee: Mork Marketing, Inc., Edgewater, MD (US)

( * ) Notice: Subject to any disclaimer, the term of this patent is extended or adjusted under 35 U.S.C. 154(b) by 0 days.

(21) Appl. No.: 10/634,310

(22) Filed: Aug. 5, 2003

(65) Prior Publication Data

US 2005/0033554 A1 Feb. 10, 2005

(51) Int. Cl.⁷ .................................................. G04F 1/00
(52) U.S. Cl. .......................................... 702/177; 705/2
(58) Field of Search ............................ 702/177; 705/2; 600/500

(56) References Cited

U.S. PATENT DOCUMENTS 5,890,128 A * 3/1999 Diaz et al. ..................... 705/2
5,989,200 A * 11/1999 Yoshimura et al. .......... 600/587
6,605,044 B2 * 8/2003 Birnbaum .................... 600/500

* cited by examiner

Primary Examiner—John Barlow
Assistant Examiner—Xiuqin Sun
(74) Attorney, Agent, or Firm—Lawrence E. Laubscher, Jr.

(57) ABSTRACT

A food and exercise calculating aid enables an individual to quickly determine how much of a selected exercise is necessary to burn off the calories consumed by a selected food item. Nutritional information for various food items and metabolic equivalent information for various exercises are stored in memories. The user accesses the memories for selected foods and exercises, as well as for the user's weight, and the aid calculates the exercise time duration necessary for the selected food.

4 Claims, 4 Drawing Sheets

FOOD AND EXERCISE CALCULATOR

BACKGROUND OF THE INVENTION

Affecting nearly seventeen million Americans, type-2 diabetes is the most prevalent form of diabetes mellitus. There are many precipitating factors involved in the cause of type-2 diabetes, but more often than not, overeating, inactivity, and consumption of unhealthy foods are the main causes of the disease. Since there is no present cure for diabetes, it becomes imperative that type-2 diabetics closely monitor their food intake, and balance this intake with exercise and physical activity in order to maintain glucose levels that are as close to normal as possible. Planning a healthy, balanced diet and exercising regularly can significantly improve the life of a person dealing with type-2 diabetes. The present invention is designed to assist in this process.

BRIEF DESCRIPTION OF THE PRIOR ART

On a daily basis, type-2 diabetics are faced with monitoring their food intake in relation to exercise activity. Although there are current diet calculators available to display the nutritional makeup of different foods, none are able to relate this nutritional data to the amount of physical activity needed to compensate for them, and burn them off. Thus, while these prior calculators can illustrate the nutritional value of certain food items, they cannot convert these values into terms that are meaningful to the user, i.e., the amount of time they will need to dedicate to exercising in order to "burn off" this food item if they are to eat it. The present invention puts the nutritional information into more concrete terms for the user. Knowing that a slice of pizza will take 36 minutes of aerobic activity to burn off is much more valuable than simply knowing that it contains 190 calories. Having this information available before eating the pizza helps an individual to better understand the actual consequences of eating it. Type-2 diabetics need to be able to access this information easily and effortlessly, on a regular basis, so that they can see the consequences of consuming various types of foods in terms of the effects on their diet and weight. Of course, all individuals, whether diabetic or not, would benefit from knowing how much exercise would be required to compensate for the food they eat in order to maintain a healthy lifestyle, proper weight, and fitness level.

SUMMARY OF THE INVENTION

The food and exercise calculating aid according to the invention includes a memory for storing nutritional information for a variety of food items and metabolic equivalent information for a variety of exercises. A controller is connected with the memory to control the selection of information to be obtained from the memory. A calculator is connected with the memory in order to calculate an exercise duration time necessary to burn the calories of a selected food item while performing the selected exercise. A display is connected with the memory and with the calculator to display the selected nutritional and metabolic equivalent information and the calculated exercise duration time.

The memory preferably comprises three portions or three separate memories. The first memory stores the nutritional information. The second memory stores the metabolic equivalent information. The third memory stores weight information which is also a factor used by the calculator for calculating the exercise duration time.

The invention also relates to an exercise calculation method for an individual. According to the method, a food item to be consumed is selected. Next, an exercise to be performed is selected. The weight of the individual is then selected following which the duration of the selected exercise is calculated for burning the calories of the selected food item for the individual. The calculation is according to the formula $$T = \text{kcal}/MET \times 3.5 \times W/200$$

where T is the exercise time, in minutes; kcal is the number of kilocalories for the selected food item; MET is the metabolic equivalent for the selected exercise; and W is the selected weight of the individual, in kilograms.

BRIEF DESCRIPTION OF THE DRAWINGS

Other objects and advantages of the invention will become apparent from a study of the following specification when viewed in the light of the accompanying drawing, in which.

DETAILED DESCRIPTION

Figure 1:
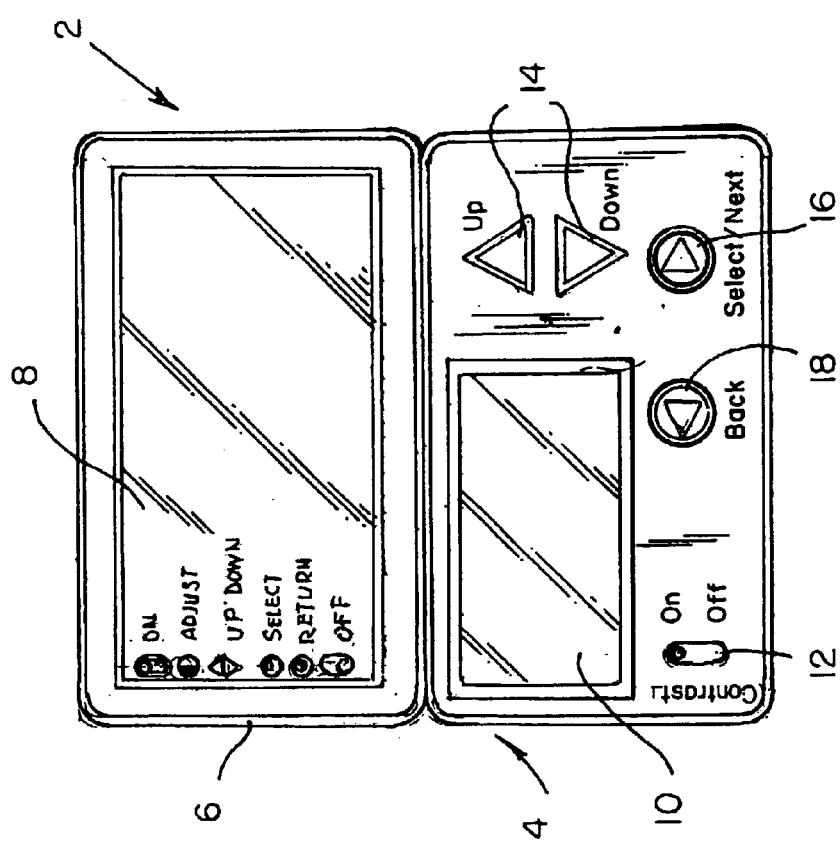

FIGS. 1–7 show the food and exercise calculating aid 2 according to the invention. Referring to FIG. 1, the calculating aid includes a housing 4 including a hinged cover 6 within which instructions 8 for operating the calculating aid are provided. On the face of the housing is a display 10, an on-off switch 12, scrolling buttons 14, a selector switch 16, and a switch 18 for going back to a previous menu. As will be developed below, FIGS. 2–8 illustrate the different information displayed on the display 10 during the operation of the calculating aid.

Figure 8:
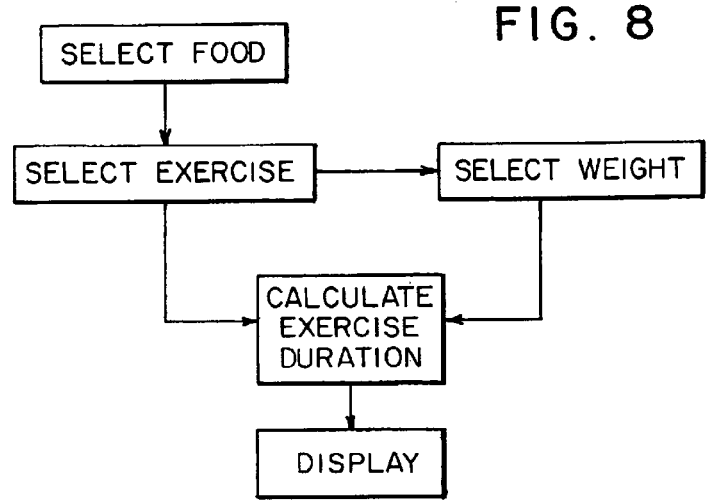
FIG. 8 is a block diagram of the sequence of steps for calculating an exercise duration according to the invention.
Figure 9:
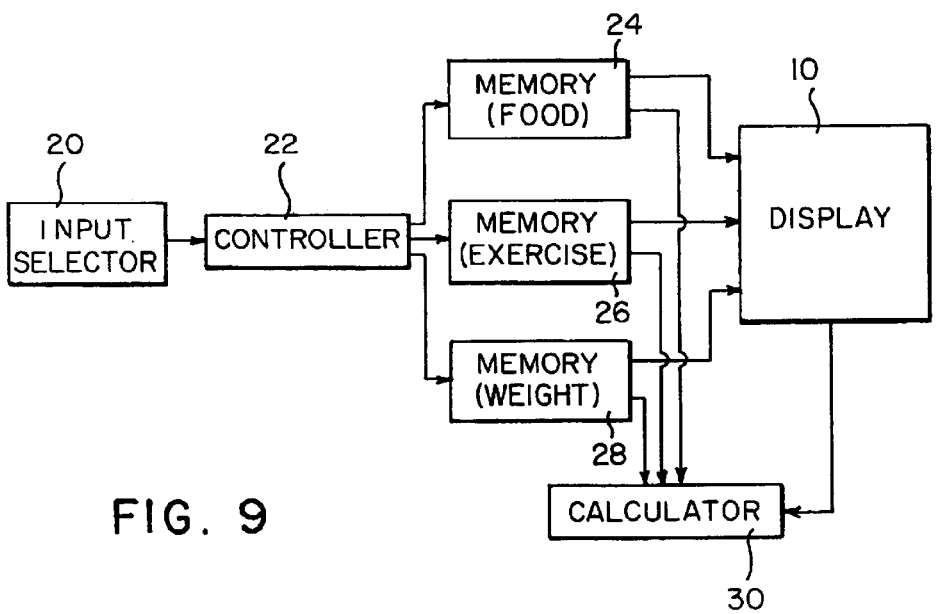
FIG. 9 is a block diagram of the food and exercise calculating aid according to the invention.

In FIG. 8 is shown the method steps for operating the calculating aid and FIG. 9 is a block diagram showing the components of the calculating aid. The input selector 20 includes the scroll, selector and back buttons shown in FIG. 1. It is used to select from the choices shown on the display 10 for various food items, exercises, and weights. A controller 22 controls which of the memories 24, 26, 28 is activated. The first memory 24 contains nutritional information for various foods. The foods are arranged by food groups within the memory 24. The second memory 26 has stored therein various exercises and the metabolic equivalents for each. The metabolic equivalent is a function of the exertion required by a particular exercise. An explanation thereof and sample metabolic equivalents for various exercises are available from the American College of Sports Medicine Guidelines for Exercise Testing and Prescriptions (Sixth Edition, 2000). The third memory 28 contains a plurality of weight ranges.

A suitable controller is the SPL 130A 128K-byte LCD controller and a suitable display is the ST 2101C dot matrix LCD driver.

The memories are connected with the display 10 to display information for a selected food, exercise and weight. A calculator 30 is connected between the memories and the display and calculates the duration of exercise time required to burn off the calories of a selected food using a selected exercise for a person of the selected weight.

Figure 2:
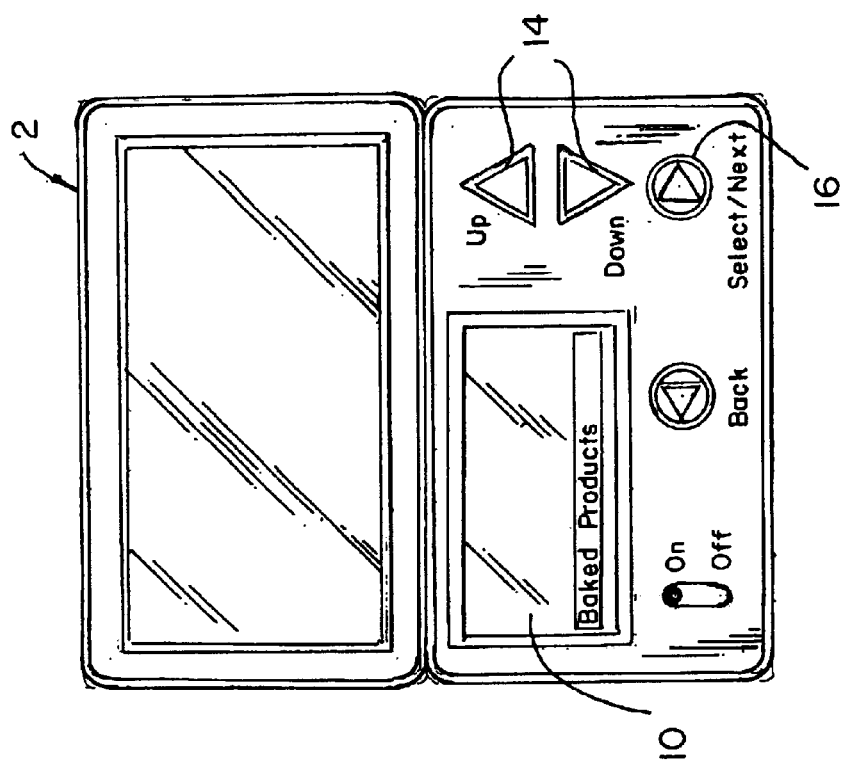
FIGS. 1–7 are plan views, respectively, of the food and exercise calculating aid according to the invention showing the information displayed to an individual during the calculation process shown in FIG. 1.

Once the aid is activated, the display prompts the selection of a food group as shown in FIG. 2. By operating the scroll buttons 14, numerous food groups are displayed. Sample food groups are displayed in Table I.

TABLE I

Food Groups

Figure 3:
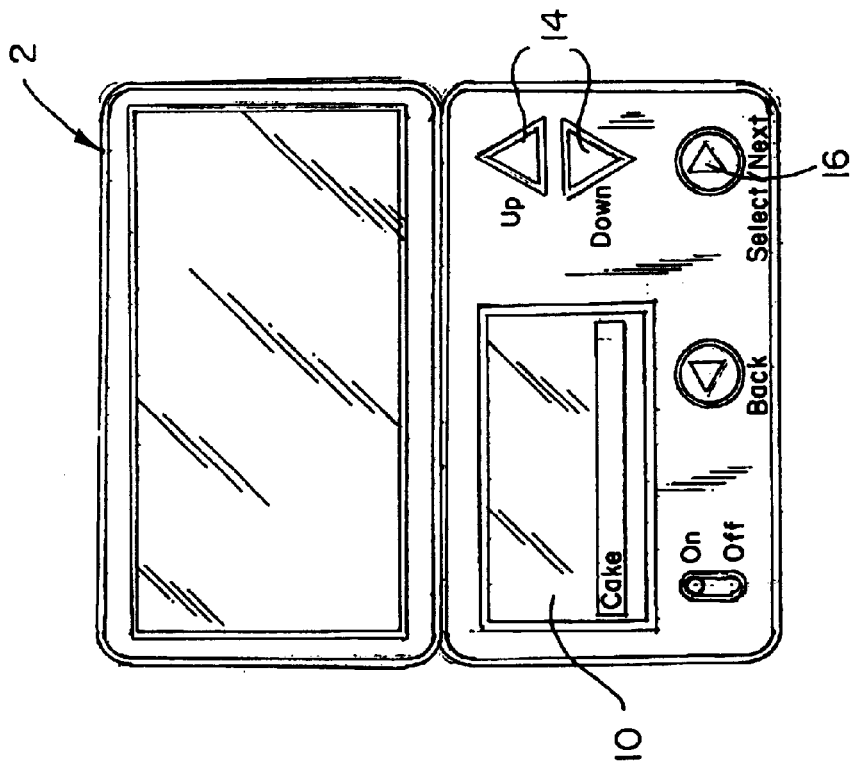

Baked Products
Beverages
Cereals
Dairy
Desserts
Restaurants
Fruits
Meals (prepared)
Meats
Seafood
Snacks
Vegetables When the desired food group is displayed and highlighted, the select button is operated and the next menu is displayed. The menu contains a list of food items for a selected group. Thus, if "Baked Products" was selected from the listed groups of FIG. 2, a list of food items from the memory 24 is displayed as shown in FIG. 3.

Tables II–VIII contain sample food items for various food groups.

TABLE II

Baked Products

Bagels
Biscuits
Bread
Bread stuffing
Cake
Cookies
Crackers
Croissants
Danish pastry
Doughnuts
English Muffins
Muffins
Pancakes
Pie (and pie crust)
Sweet rolls
Toaster pastries
Tortillas

TABLE III

Cereals

Kelloggs
Quaker
General Mills
Malt-O-Meal
Cream of Wheat (also Cream of Rice)
Post (Kraft)
Other (Heartland Natural Cereal, Maypo, Ralson, Wheatena, Maltex, Roman Meal, etc.)

TABLE IV

Restaurants

Arby's
Boston Market

TABLE IV-continued

Restaurants

Bruegger's Bagels
Burger King
Dairy Queen
Denny's
KFC
Krispy Kreme
Leeann Chinn
McDonalds
Olive Garden
Pizza Hut
Red Lobster
Subway
Taco Bell

TABLE V

Fruits and Fruit Juices

Avocados
Apples and apple products (apple juice, applesauce)
Apricots
Bananas
Berries (blackberries, blueberries, boysenberries, strawberries, raspberries)
Cherries
Fruit salad and fruit cocktails
Grapefruit and grapefruit juice
Grapes and grape juice
Melons
Oranges and tangerines, fruits and juices
Peaches
Pears
Pineapple
Prunes and prune juice
Other (kiwi fruit, currants, rhubarb)

TABLE VI

Meals (prepared)

Banquet
Budget Gourmet
Chef Boyardee
Hormel
Hot Pockets
Kraft
Marie Callender's
Nestle, Chef-Mate
Stouffers
Sunny Fresh
Weight Watchers
Worthington Foods/Morningstar Farms
Other (Jimmy Dean, Nalley, Red Baron, Tyson, Stagg, etc.)

TABLE VII

Desserts

Candies, Hershey
Candies, M&M Mars
Candies, Nestle
Candies, other
Frostings
Frozen desserts
Gelatins
Gum
Honey and molasses
Jams and jellies (including marmalade and fruit butters)
Puddings, custards and flan

TABLE VII-continued

Desserts

Syrups
Toppings
Other (sugar, sweeteners, pie filling, fruit leather, etc.)

TABLE VIII

Snacks

Fruit snacks and Fruit Roll-Ups
Granola bars (including Kudos)
Popcorn
Potato chips
Pretzels (including Combos)
Rice cakes
Tortilla chips
Trail mix
Other (beef jerky, corn-based items, Corn Nuts, Chex Mix, Sesame Sticks, Nutri-Grain bars, Rice Krispie Treats, etc.)

The above tables contain only representative samples of food groups and items. Any number of additional items may be included and the grouping of items can be altered as desired.

Figure 4:
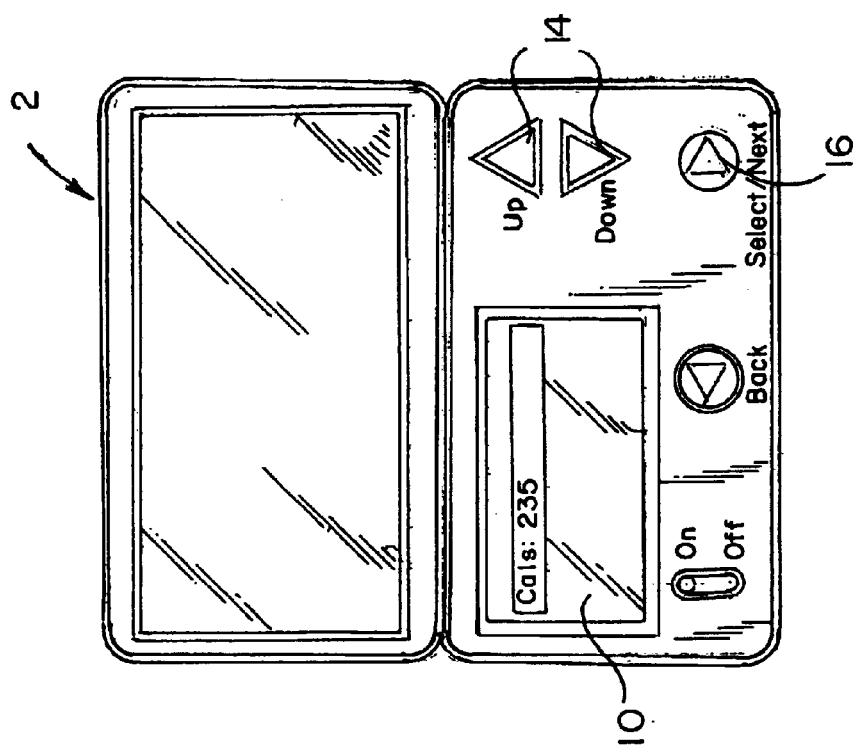

When the desired food item is displayed (FIG. 3), the select button is activated to obtain from the food memory 24 the nutritional information for the item. The nutritional information is automatically displayed on the display 10 as shown in FIG. 4 and sent to the calculator 30. The nutritional information includes calories per serving, carbohydrates (in grams), carbohydrate choices, fats (in grams), and proteins (in grams). The typical portion or serving size is also provided. The carbohydrate choices are automatically calculated by the calculator 30 based on the number of grams of carbohydrates in the food item using the following formula:

Carbohydrate Choices=Carbohydrates (grams)÷15

Figure 5:
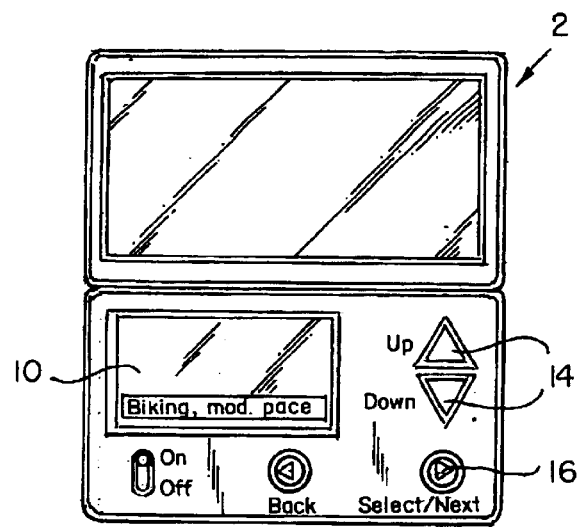

After the nutritional information has been displayed, the selector button is activated and the controller 22 accesses the second memory 26 to display various exercises as shown in FIG. 5. Examples of exercises are set forth in table IX.

TABLE IX

Exercises

Aerobics
Basketball
Bicycling (5.5 mph)
Bicycling (13 mph)
Bowling
Dancing
Gardening
Golfing
Jogging (5.5 mph)
Jogging (8 mph)
Martial/kickbox
Mowing lawn
Shoveling snow
Tennis/handball
Walking (2 mph)
Walking (4 mph)
Weightlifting
Yoga/stretching The user scrolls through the exercise menu using the scroll buttons 14 until the desired exercise is highlighted. Activation of the select button 16 sends metabolic equivalent information for the selected exercise to the calculator 30.

Figures 6, 7:
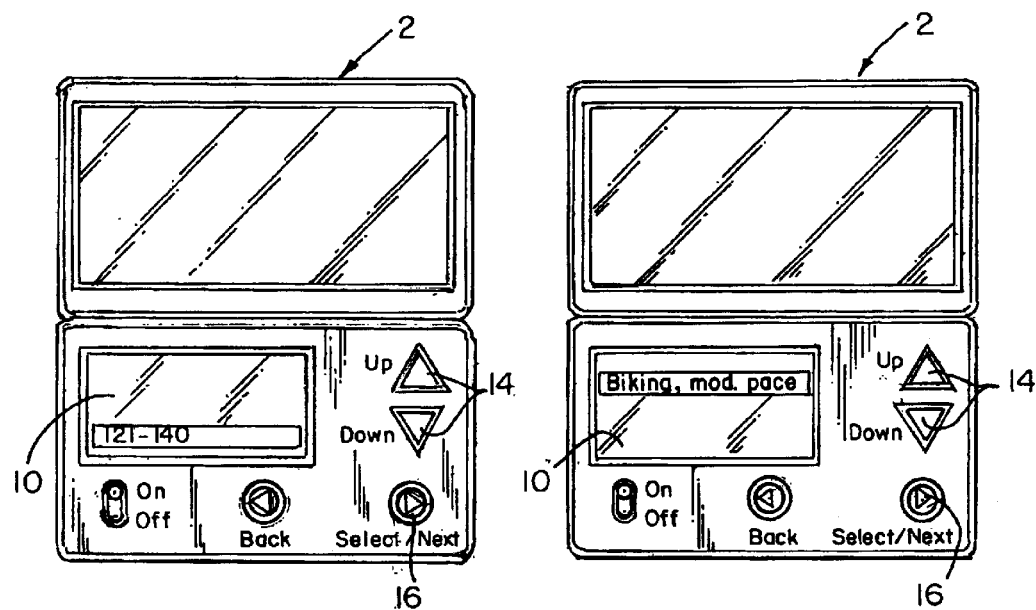

Next, the weight range information from the third memory 28 is displayed on the display 10 as shown in FIG. 6. The weight ranges are scrolled by operation of scroll buttons 14 until the weight range for the user is displayed. Operation of the select button sends the weight range information to the calculator 30.

The calculator 30 calculates an exercise duration time necessary for the individual to burn off the calories associated with the selected food item by performing the selected exercise using the formula $$T = kcal/MET \times 3.5 \times W/200$$

where T is the exercise time in minutes, kcal is the number of kilocalories for the selected food item, MET is the metabolic equivalent for the selected exercise and W is the selected weight, in kilograms, of the individual. The calculated duration time for the exercise is displayed on the display as shown in FIG. 7.

A less accurate, but still valuable, calculation of the exercise duration time can be obtained by omitting the weight factor from the equation or by using a default value such as 150 pounds The diet and exercise calculator according to the invention benefits many individuals involved in caring for those with type-2 diabetes as well as the patients themselves. Family members of diabetics, or those who are at risk of developing type-2 diabetes would benefit from the calculator as well. Diabetic educators and physicians can use the product to help educate and inform those at risk to help them change their unhealthy habits before they actually develop the disease. The general public would also find the calculator to be useful in their attempts to live a healthy lifestyle. The diet and exercise calculator allows people to view the consequences of eating certain FDA categorized foods prior to consumption, and relate this to a specific physical activity. The calculator displays the nutritional information and calculates the amount to time it will take, while performing a selected activity, to burn off the fat and calories of a selected food item.

While the preferred forms and embodiments of the invention have been illustrated and described, it will be apparent to those of ordinary skill in the art that various changes and modification may be made without deviating from the inventive concepts set forth above.

What is claimed is:

1. An exercise calculation method for an individual, comprising the steps of:
   (a) selecting a food item to be consumed;
   (b) selecting an exercise to be performed;
   (c) selecting a weight for the individual; and
   (d) calculating the duration of exercise necessary to burn off the calories of the food item after consumption by the individual according to the formula $$T = kcal/MET \times 3.5 \times W/200$$

where T is the exercise time, in minutes; kcal is the number of kilocalories for the selected food item; MET is the metabolic equivalent for the selected exercise; and W is the selected weight of the individual, in kilograms.

2. A food and exercise aid, comprising:
   (a) a memory for storing nutritional information for a variety of food items, metabolic equivalent information for a variety of exercises, and the weight of an individual;

(b) a controller connected with said memory for controlling the selection of information to be obtained from said memory;

(c) a calculator connected with said memory for calculating an exercise duration time necessary to burn the calories of a selected food item via a selected exercise according to the formula $$T = kcal/MET \times 3.5 \times W/200$$

where T is the exercise time, in minutes; kcal is the number of kilocalories for the selected food item; MET is the metabolic equivalent for the selected exercise; and W is the selected weight of the individual, in kilograms; and (d) a display connected with said memory and with said calculator for displaying the nutritional and metabolic equivalent information and the calculated exercise duration time.

3. A food and exercise aid as defined in claim 2, wherein said memory comprises a food memory for storing the nutritional information, an exercise memory for storing the metabolic equivalent information and a weight memory for storing the weight information.

4. A food and exercise aid as defined in claim 3, and further comprising an input selector connected with said controller for selecting a food item, an exercise and a weight from said food, exercise and weight memories, respectively.

* * * * *